United States Patent
Thompson et al.

[11] Patent Number: 5,457,895
[45] Date of Patent: Oct. 17, 1995

[54] METHOD OF IDENTIFYING FREEZE-DRIED DOSAGE FORMS

[75] Inventors: Andrew R. Thompson, Swindon; Richard J. Yarwood, Buckland; Patrick Kearney, Swindon, all of Great Britain

[73] Assignee: R. P. Scherer Corporation, Troy, Mich.

[21] Appl. No.: 104,486

[22] Filed: Oct. 1, 1993

[51] Int. Cl.[6] .................................................. F26B 5/06
[52] U.S. Cl. ................................................ 34/296; 34/297
[58] Field of Search ....................................... 34/296, 297

[56] References Cited

U.S. PATENT DOCUMENTS

| | | |
|---|---|---|
| 510,453 | 12/1893 | Tobin . |
| 2,645,852 | 8/1948 | Weinberg . |
| 3,125,490 | 5/1964 | Hershberg . |
| 3,534,440 | 10/1970 | Roberts . |
| 4,305,502 | 12/1981 | Gregory et al. ............ 206/532 |

OTHER PUBLICATIONS

International Search Report Dated Feb. 6, 1995, in International Application No. PCT/US94/10831.
International Publication No. WO 91/09591 (International Application No. PCT/US90/07319.
International Publication No. 0450 141 A1.
International Publication No. WO 93/12770 (International Application No. PCT/US92/09273.
International Publication No. WO 94/12142 (International Application No. PCT/GB93/02459).

Primary Examiner—Henry A. Bennet
Assistant Examiner—Siddharth Ohri
Attorney, Agent, or Firm—Banner & Allegretti, Ltd.

[57] ABSTRACT

The invention permits the application of an identifying mark onto a freeze-dried tablet without the need for application of pressure or for printing directly on the tablet. The invention comprises the preparation of a freeze-dried unit that is embossed with an identifying mark such as a manufacturer's logo, medicinal component strength, or other information relating to the unit. The desired identifying mark is first embossed onto the base of a container such as a blister pocket. Liquid suspension is then filled into the container and freeze-dried therein. The resulting freeze-dried unit in the container is thereby embossed with substantial copy of the identifying mark that was embossed on the base of the container. The embossed identifying mark on the base of the container remains thereon as well, providing at reduced manufacturing cost the added ability to learn the identifying mark on the enclosed freeze-dried unit without opening the blister pack.

18 Claims, 2 Drawing Sheets

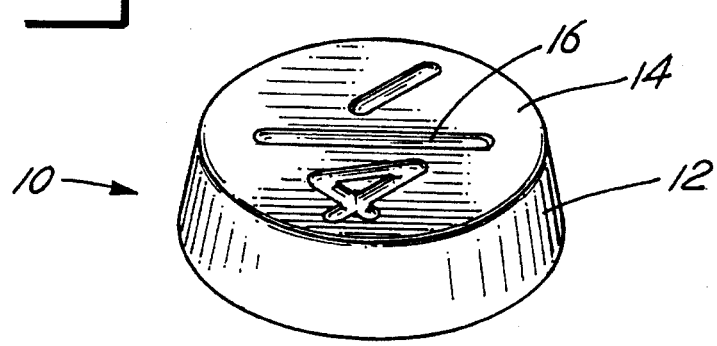
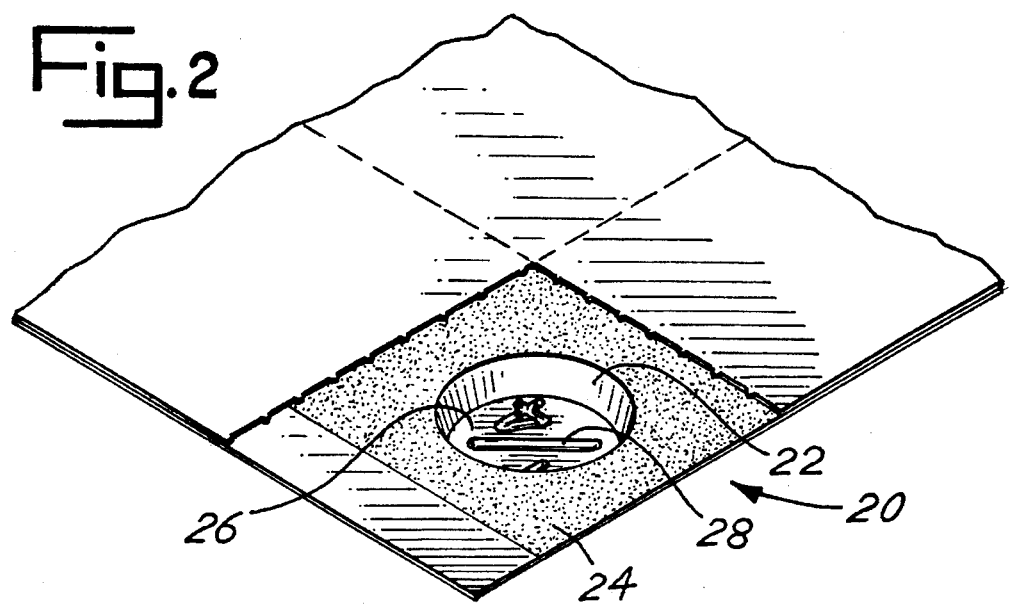
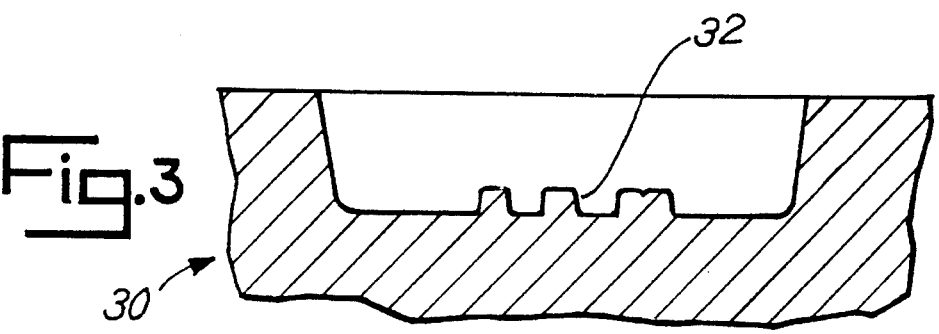

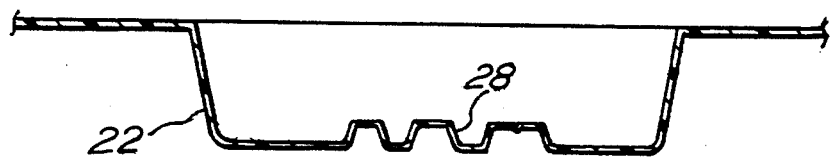
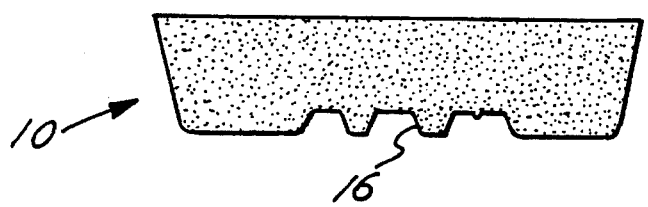
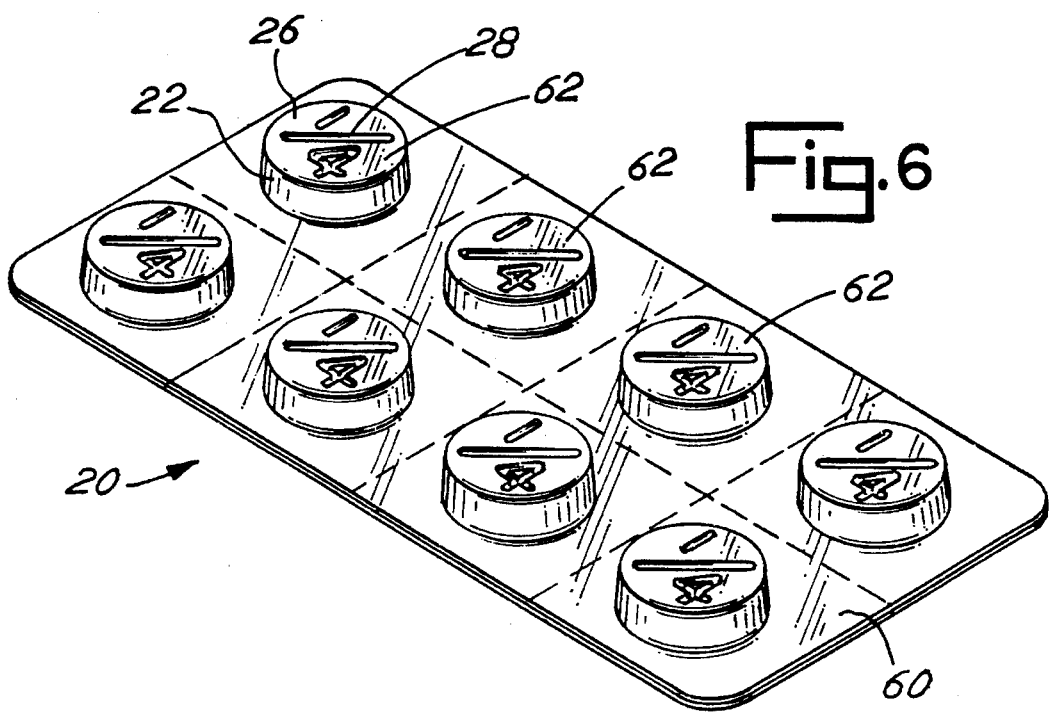

METHOD OF IDENTIFYING FREEZE-DRIED DOSAGE FORMS

BACKGROUND OF THE INVENTION

The present invention relates to the identification of freeze-dried dosage forms. More particularly, the present invention relates to the embossment of porous freeze-dried dosage forms by embossing the base of a blister pocket and forming a freeze-dried unit in the embossed blister pocket, whereby the embossment on the blister pocket is transferred to the dosage form during the freeze-drying process.

Medication in forms such as tablets, capsules, caplets or freeze-dried dosage forms has been typically packaged in blister packages or sheets of multiple blister pockets or compartments. A base sheet of transparent or opaque plastic, for instance polyvinyl chloride (PVC or PVC type laminates), will frequently have a plurality of blister pockets projecting from one face thereof, for containing the unit dosages of medication.

If the units of medication to be packaged in the blister package are solid units such as tablets, capsules or caplets, the solid units may simply be deposited into the blister pockets of the base sheet. On the other hand, if the units to be packaged are freeze-dried dosage forms, then the medication may be closed and frozen directly within the blister pockets and then dried therein using a freeze-drying process, as explained by Gregory et al., U.S. Pat. No. 4,305,502. The freeze-drying process is well known in the art and may involve first dosing a liquid suspension into the pre-formed blister pockets of the base sheet. The base sheet containing the suspension is then cooled by a medium such as liquid nitrogen or carbon dioxide, thereby freezing the contents of the blister pockets. The frozen contents may then be subjected to reduced pressure to complete the freeze drying process.

The pharmaceutical industry abounds with a variety of dosage forms, many of which are very similar, if not identical, to each other in outward appearance. It is therefore often necessary to place an identifying logo, code or other mark on each individual dosage form. Such mark might identify the manufacturer, the brand name, the active component strength or any other useful information regarding the dosage form. Further, several states in the United States of America currently require certain identifying markings to appear on individual units of medication.

Solid units of medication such as tablets, capsules or caplets have been acceptably identified by printing information directly onto the unit. Alternatively, solid units have been embossed with an identifying mark by compressing an embossment into the surface of the unit. The latter method is illustrated by or analogous to the processes disclosed by U.S. Pat. Nos. 3,534,440 (Roberts), 2,645,852 (Weinberg) and 510,453 (Tobin).

The Roberts patent "relates to the manufacture of bodies of materials formable by pressing, more particularly but not exclusively soap and synthetic detergent bars, tablets and the like." (Col. 1, lines 29–32). In particular, the Roberts patent teaches a process that incorporates an apparatus comprised of (1) a lower die having a cavity, the planar bottom surface of the cavity serving as a lower "pressing face," and (2) an upper die whose planar underside serves as an upper "pressing face." A strip of thin embossed material is affixed to either the lower pressing face or the upper pressing face (or both). The body of material to be formed and embossed is then placed into the cavity, and the upper and lower dies are "brought together under positive pressure until [the] die surfaces... abut. [The body] is thereby shaped to final form and at the same time its upper [and/or lower] surface engaged by [the embossed strip] is formed with indented indicia corresponding to the projecting characters... on the embossed strip." (Col. 3, lines 59–65).

The Weinberg patent teaches a device for the manufacture of "pats or chips from a block of butter, oleomargarine, or the like soft, plastic, easily incisible material." The device generally comprises a base having upwardly extending walls or flanges, a cover telescopically but loosely fitting over the base, and an "impressor" plate removably mounted within the cover. The base and cover are made of metal or, preferably, plastic capable of being warmed sufficiently to prevent the cover and base from sticking to the butter. The impressor plate may be "formed with ribs for dividing the slab [of butter] into a plurality of separate pats or chips for impressing a design into the several pats." (Col. 1, lines 14–17). Butter is placed in the base, and the cover is positioned and pressured down, thereby causing the impressor plate to emboss a given design onto the butter.

Tobin discloses a butter molding machine, "the purpose of [which] is to provide improved mechanism for rapidly molding butter, or similar substance, into small disks or 'pats.'" (Col 1, lines 10–13). In general, the invention is comprised of (1) an upright cylinder that is charged with butter, the cylinder having a mouth at its top for emitting the butter, and a piston disposed in the cylinder for forcing the butter out of the mouth; and (2) a plate having one or more mold cavities to be filled with butter emitted from the mouth of the cylinder and to impart a shape and pattern to the resulting butter pats. Upward pressure is applied to the piston to force the butter out of the mouth of the cylinder and into the mold cavities. "[T]he pressure upon the piston is made sufficient to produce the complete imprint of the dies upon each pat of butter thus molded." (Col 5, lines 10–13).

While the above-illustrated printing and direct compression methods are well suited to the application of an identifying mark to most solid units of medication, such methods are ill-suited to applying an identifying mark to porous freeze-dried units. In particular, it has been determined that, due to the inherent fragility, surface undulation, moisture sensitivity and chemical makeup of freeze-dried dosage forms, the application of compression would cause deformation, reduced porosity and hence increased dispersion time, and possibly cracking of the dosage forms. Similarly, it is believed that the chemical makeup, moisture sensitivity, porosity and surface undulation of freeze dried dosage forms would cause ink to dissolve the dosage forms at the point of contact or to diffuse throughout the dosage forms leading to clarity problems. A need therefore exists for a method of applying an identifying mark to the surface of freeze-dried pharmaceutical units.

Accordingly, it is a primary objective of the present invention to provide a method of identifying freeze-dried dosage forms.

It is another objective of the present invention to provide a method of applying an identifying mark to a freeze-dried unit during the freeze-drying process.

It is yet another objective of the present invention to provide a method of preparing an embossed freeze-dried dosage form without cracking or otherwise deforming or dissolving the dosage form.

It is a further objective of the present invention to provide a method of embossing a freeze-dried unit of medication during the process of freeze-drying the unit in a blister pocket.

It is still a further objective of the present invention to provide a reduced cost method of manufacturing a combination of an embossed blister pocket and an embossed freeze-dried unit contained in the blister pocket.

Further objects and advantages of the present invention will become apparent in the following description.

SUMMARY OF THE INVENTION

The present invention provides a method for embossing freeze-dried dosage forms directly in blister pockets during the freeze-drying process. In particular, a desired logo or other product information is first embossed or otherwise formed into the base of a blister pocket in which the freeze-dried unit will be formed. An appropriate dose of a medicated liquid suspension is filled into the embossed blister pocket. The blister pocket containing the suspension is then cooled by a medium such as liquid nitrogen or carbon dioxide, thereby freezing the contents of the blister pocket. Finally, freeze-drying is completed by subjecting the contents to reduced pressure. During the freeze-drying process, the embossment on the base of the blister pocket is copied to the adjacent base of the dosage form. Further, the original identifying embossment remains on the blister pocket as well, thereby providing the same useful identification on the exterior surface of the blister package.

DETAILED DESCRIPTION OF THE DRAWINGS

There is shown in the attached drawings a preferred embodiment of the present invention, wherein like numerals in the various views refer to like elements and wherein:

FIG. 1 is a perspective view showing an embossed freeze-dried unit made in accordance with the present invention.

FIG. 2 is a perspective top view showing a portion of a blister package having at least one embossed blister pocket.

FIG. 3 is a side elevational view of a portion of a machine tool bearing a code to be embossed to a plastic blister pocket web during a thermoforming process in accordance with the present invention.

FIG. 4 is a side elevational view of an embossed blister pocket thermoformed in the machine tool of FIG. 3.

FIG. 5 is a side elevational view of an embossed freeze-dried dosage form prepared in the embossed blister pocket of FIG. 4.

FIG. 6 is a perspective view of the base of a blister package showing the embossments that are copied to the enclosed freeze-dried dosage forms.

DETAILED DESCRIPTION OF THE PREFERRED EMBODIMENT

FIG. 1 is a perspective view showing an embossed freeze-dried unit 10 made in accordance with the present invention. The freeze-dried unit 10 comprises a body 12 and a base 14. For illustrative purposes, unit 10 is shown with its base 14 on the top. The base 14 of the unit is embossed with an identifying mark or embossment 16. While FIG. 1 illustrates the embossment of the identifying mark "1/4" on the base of the unit, the present invention is not limited to this or any other particular choice of identifying mark. In the preferred embodiment, the freeze-dried unit of the present invention may be embossed with any desired identifying mark 16. For instance, it may be useful to prepare a freeze-dried pharmaceutical tablet that is embossed with a manufacturer's logo, a brand name, the component strength or any other information regarding the tablet. The embossment 16 may comprise a marking that either protrudes outwardly from the surface of the base 14, that protrudes inwardly from the surface of the base 14, or that is a combination of both outward and inward protrusions. The invention is not limited to a particular type of embossment.

FIG. 2 illustrates a perspective top view of a portion of a blister package 20. Illustrated in particular is an embossed blister pocket 22 recessed in the blister package 20. The blister pocket 22 may be one of a plurality of such pockets arranged in the blister package 20. The blister package 20 accordingly comprises a blister sheet 24 and at least one recessed blister pocket 22. The interior surface or base 26 of the blister pocket 22 is embossed with an identifying mark or embossment 28. The embossment on the base 26 of the blister pocket is substantially the reverse of the desired embossment 16 on the base 14 of the freeze-dried unit 10. While, in the preferred embodiment, the embossment 28 is formed on the base of the blister pocket, the present invention contemplates one or more embossed identifying marks formed on any of the interior surfaces of the blister pocket.

FIGS. 3 and 4 illustrate in part the thermoforming of an embossed blister pocket in accordance with the present invention. FIG. 3 illustrates a side elevational view of a machine tool 30 bearing a raised (or lowered) identifying mark 32. The machine tool 30 is used to thermoform by known processes an embossed blister pocket 22, an example of which is illustrated by the side elevational view of FIG. 4. The raised identifying mark 32 on the machine tool 30 is thereby substantially identical to the embossed identifying mark 28 on the base surface of the blister pocket 22.

FIG. 5 illustrates the side elevational view of a freeze-dried unit 10 formed in the embossed blister pocket 22 in accordance with the present invention. The freeze-dried unit may be prepared by any known process of freeze-drying, such as that disclosed by the Gregory et al. patent, U.S. Pat. No. 4,305,502. For instance, the process may comprise first dosing aliquots of liquid suspension containing active medicament directly into the embossed blister pocket 22. At least a portion of the liquid suspension is thereby in contact with the embossed identifying mark 28 on the base 26 of the blister pocket. The blister pocket 22 or entire blister package 20 containing the liquid suspension is then cooled by application of a medium such as liquid nitrogen or carbon dioxide, thereby freezing the contents of the blister pocket. Finally, the frozen contents are preferably subjected to reduced pressure to complete the freeze-drying process. The result is a porous freeze-dried unit 10 having an embossment 16 that coincides substantially with the embossment 28 on the base 26 of the blister pocket 22, the porous freeze-dried unit being contained within the embossed blister pocket.

The process of the preferred embodiment, while not intended to be limited to a specific order of steps, can thus be summarized as follows. First, a blister pocket is accurately thermoformed or otherwise formed to bear an embossed identifying mark on its interior surface (and correspondingly on its exterior surface). Next, a liquid suspension is filled into the blister pocket, such that at least a portion of the liquid suspension is in contact with the embossed identifying mark on the interior surface of the blister pocket. The blister pocket containing the suspension is then subjected to freezing temperature and reduced pressure to thereby freeze-dry the contents. A porous freeze-dried unit results in the blister pocket, bearing an embossment substantially identical to the embossment on the blister pocket. In the preferred embodiment, a cover sheet is adhered to the blister sheet to enclose the embossed freeze-dried unit in the embossed blister pocket.

It will be understood by those skilled in the art that the present invention is not limited to the use of embossed blister pockets or blister packaging to prepare the embossed freeze-dried units. Various other embossed or embossable containers may be used as well.

Finally, FIG. 6 illustrates an added advantage of the present invention. Shown in FIG. 6 is a perspective view of the bottom surface 60 of a blister package 20 containing embossed freeze-dried units in accordance with the present invention. Projecting from the bottom surface of the blister package are the exterior surfaces 62 of a plurality of blister pockets 22. Pursuant to the present invention, the base 26 of each blister pocket 22 has been embossed with an identifying mark 28 that is substantially identical to the identifying marks 16 embossed on each respective enclosed freeze-dried unit 10. Thus, the identifying mark of a given freeze-dried unit will be visible as well on the exterior surface of the blister pocket in which the freeze-dried unit is contained. This feature may provide useful information to assist in the proper dispensing of pharmaceuticals without the need for first opening the blister package containing the pharmaceutical.

While a preferred embodiment of the present invention has been depicted and described, it will be appreciated by those skilled in the art that many modifications, substitutions and changes may be made thereto without departing from the true spirit and scope of the invention.

What is claimed is:

1. A method of applying an identifying mark to a fast-dissolving dosage form, comprising:

forming a blister pocket having at least one generally continuous blister pocket surface bearing an identifying embossment, said identifying embossment being discernable from said generally continuous blister pocket surface and representing a dosage identifying mark; and forming said fast-dissolving dosage form directly in said blister pocket such that said fast-dissolving dosage form includes a generally continuous dosage surface corresponding to said generally continuous blister pocket surface and a tactile embossed identifying mark thereon corresponding to said identifying embossment.

2. A method as claimed in claim 1, wherein the step of forming said fast-dissolving dosage form comprises freeze-drying a liquid suspension in said blister pocket.

3. A method as claimed in claim 1, wherein said tactile embossed identifying mark is an elevated identifying mark.

4. A method as claimed in claim 1, wherein said tactile embossed identifying mark is a depressed identifying mark.

5. A method as claimed in claim 1, wherein the step of forming said blister pocket comprises thermoforming.

6. A method as claimed in claim 1, wherein the step of forming said blister pocket comprises cold-forming.

7. A method as claimed in claim 1 wherein said blister pocket comprises aluminum laminate.

8. A method as claimed in claim 1 wherein said blister pocket comprises plastic laminate.

9. A fast-dissolving dosage form bearing an embossed identifying mark applied by a process as claimed in claim 1.

10. A method as claimed in claim 1, wherein said dosage identifying mark comprises indicia of component strength of said fast dissolving dosage form.

11. A method as claimed in claim 1, wherein said dosage identifying mark comprises indicia of a manufacturer of said fast dissolving dosage form.

12. A combination comprising (i) a blister pocket having a generally continuous blister pocket surface embossed with an identifying embossment and (ii) a fast-dissolving dosage form contained in said blister pocket having a generally continuous dosage surface bearing a tactile embossed identifying mark corresponding to said identifying embossment, said tactile embossed identifying mark being applied to said generally continuous dosage surface by a process as claimed in claim 11.

13. A fast dissolving dosage form formed in a blister pocket and bearing an overall shape defined by the shape of the blister pocket including at least one generally continuous dosage surface formed by contact with a corresponding generally continuous blister pocket surface, said fast dissolving dosage form comprising:

a predetermined tactile identifying mark embossed on said generally continuous dosage surface formed by contact with a substantially identical embossment on said generally continuous blister pocket surface, said predetermined tactile identifying mark being three-dimensionally discernable from said generally continuous dosage surface.

14. A fast dissolving dosage form as claimed in claim 13, wherein said fast dissolving dosage form is freeze-dried in said blister pocket.

15. A fast dissolving dosage form as claimed in claim 13, wherein said predetermined tactile identifying mark comprises an elevated embossment.

16. A fast dissolving dosage form as claimed in claim 13, wherein said predetermined tactile identifying mark comprises a depressed embossment.

17. A fast dissolving dosage form as claimed in claim 13, wherein said predetermined tactile identifying mark comprises indicia of component strength of said fast dissolving dosage form.

18. A method as claimed in claim 13, wherein said predetermined tactile identifying mark comprises indicia of a manufacturer of said fast dissolving dosage form.

\* \* \* \* \*

UNITED STATES PATENT AND TRADEMARK OFFICE
CERTIFICATE OF CORRECTION

PATENT NO. : 5,457,895

DATED : October 17, 1995

INVENTOR(S) : Andrew R. Thompson; Richard J. Yarwood; Patrick Kearney

It is certified that error appears in the above-identified patent and that said Letters Patent is hereby corrected as shown below:

At column 6, line 24, the phrase "in claim 11" should read --in cliam 1--;
At column 6, line 51, the phrase "a method" should read --a fast dissolving dosage form--.

Signed and Sealed this

Thirty-first Day of August, 1999

Attest:

Q. TODD DICKINSON

*Attesting Officer*     *Acting Commissioner of Patents and Trademarks*